US006859032B2

(12) United States Patent
Heaton et al.

(10) Patent No.: US 6,859,032 B2
(45) Date of Patent: Feb. 22, 2005

(54) METHOD FOR DETERMINING MOLECULAR PROPERTIES OF HYDROCARBON MIXTURES FROM NMR DATA

(75) Inventors: Nicholas J. Heaton, Houston, TX (US); Robert Freedman, Houston, TX (US)

(73) Assignee: Schlumberger Technology Corporation, Sugar Land, TX (US)

(*) Notice: Subject to any disclaimer, the term of this patent is extended or adjusted under 35 U.S.C. 154(b) by 78 days.

(21) Appl. No.: 10/029,698

(22) Filed: Dec. 18, 2001

(65) Prior Publication Data

US 2003/0128032 A1 Jul. 10, 2003

(51) Int. Cl.[7] ............................................. G01V 3/00
(52) U.S. Cl. ....................................................... 324/303
(58) Field of Search ................................. 324/300–303, 324/363

(56) References Cited

U.S. PATENT DOCUMENTS

| | | | |
|---|---|---|---|
| 3,597,681 A | | 8/1971 | Huckabey et al. |
| 4,710,713 A | | 12/1987 | Strikman |
| 4,717,876 A | * | 1/1988 | Masi et al. .................. 324/303 |
| 4,717,877 A | * | 1/1988 | Taicher et al. .............. 324/303 |
| 4,717,878 A | * | 1/1988 | Taicher et al. .............. 324/303 |
| 4,792,757 A | * | 12/1988 | Vail et al. .................... 324/303 |
| 5,055,788 A | | 10/1991 | Kleinberg et al. |
| 5,291,137 A | | 3/1994 | Freedman |
| 5,306,640 A | * | 4/1994 | Vinegar et al. ................ 436/29 |
| 5,309,098 A | * | 5/1994 | Coates et al. ................ 324/303 |
| 5,412,320 A | * | 5/1995 | Coates ........................ 324/303 |
| 5,557,200 A | * | 9/1996 | Coates ........................ 324/303 |
| 5,696,448 A | * | 12/1997 | Coates et al. ................ 324/303 |
| 5,936,405 A | * | 8/1999 | Prammer et al. ............ 324/303 |
| 6,084,408 A | * | 7/2000 | Chen et al. .................. 324/303 |
| 6,107,796 A | * | 8/2000 | Prammer .................... 324/303 |
| 6,111,408 A | * | 8/2000 | Blades et al. ................ 324/303 |
| 6,111,409 A | * | 8/2000 | Edwards et al. ............ 324/303 |
| 6,140,817 A | | 10/2000 | Flaum et al. |
| 6,229,308 B1 | * | 5/2001 | Freedman .................... 324/303 |
| 6,242,912 B1 | * | 6/2001 | Prammer et al. ........... 324/303 |
| 6,337,568 B1 | * | 1/2002 | Tutunji et al. .............. 324/303 |
| 6,346,813 B1 | * | 2/2002 | Kleinberg .................... 324/303 |
| 6,424,919 B1 | * | 7/2002 | Moran et al. .................. 702/6 |

FOREIGN PATENT DOCUMENTS

| | | |
|---|---|---|
| JP | 2002 014063 | 1/2002 |
| WO | WO 03/016951 A1 | 2/2003 |

OTHER PUBLICATIONS

R. Freedman et al., "A New NMR Method of Fluid Characterization in Reservoir Rocks: Experimental Confirmation and Simulation Results," *SPE 63214*, SPE Annual Technical Conference and Exhibition, Dallas TX (Oct. 1–4, 2000).

(List continued on next page.)

Primary Examiner—Diego Gutierrez
Assistant Examiner—Dixomara Vargas
(74) Attorney, Agent, or Firm—Kevin P. McEnaney; Brigitte L. Echols

(57) ABSTRACT

A method for determining a molecular property of each constituent in a mixture of hydrocarbons includes deriving at least one dynamic parameter for each constituent in the mixture from NMR data measured on the mixture; and calculating the molecular property for the each constituent in the mixture from the at least one dynamic parameter for each constituent. The step of deriving the at least one dynamic parameter may include generating a model that includes a plurality of components for the constituents of the mixture and iteratively modifying the model components to optimize the model with respect to the NMR data. The at least one dynamic parameter includes a parameter selected from the group consisting of a longitudinal relaxation time, a transverse relaxation time, a ratio of longitudinal to transverse relaxation time, and a diffusion rate.

31 Claims, 5 Drawing Sheets

OTHER PUBLICATIONS

S. Meiboom and D. Gill, "Modified Spin–Echo Method for Measuring Nuclear Relaxation Times," *Rev. Scientific Instruments* 29, pp. 688–691 (1958).

C.E. Morriss et al., "Hydrocarbon Saturation and Viscosity Estimation from NMR Logging in the Belridge Diatomite," *SPWLA*, 35th Annual Logging Symposium (Jun. 19–22, 1994).

McCain, Wm D. Jr., "Components of Naturally Occurring Petroleum Fluids," *The Properties of Petroleum Fluids* 2nd Ed., Ch. 1, pp. 1–45 (1990).

S–W Lo et al., "Relaxation Time and Diffusion Measurements of Methane and n–Decane Mixtures," The Log Analyst, pp. 43–47(Nov.–Dec. 1998).

A. Bondi, "Viscosity," *Physical Properties of Molecular Crystals, Liquids, and Glasses*, Chapter 12, pp. 348–349 (John Wiley & Sons, Inc., New York, NY (1968).

N. Bloembergen et al., "Relaxation Effects in Nuclear Magnetic Resonance Absorption," *Physical Review*, vol. 73 No. 7, pp. 679–712 (1948).

H Barjat et al., "High Resolution Diffusion–Ordered 2D Spectroscopy (HR–DOSY)—A New Tool for the Analysis of Complex Mixtures," *J. Magnetic Res.* Series B 108, pp. 170–172 (1995).

OL Gulder, "Influence of Hydrocarbon Fuel Structural Constitution and Flame Temperature on Soot Formation in Laminar Diffusion Flames," *Combustion and Flame* 78, pp. 179–194 (1989).

* cited by examiner

FIG. 4
(PRIOR ART)
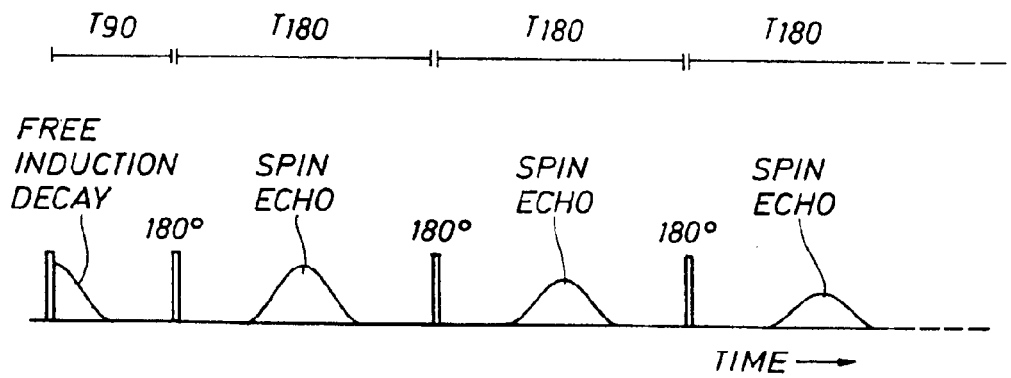
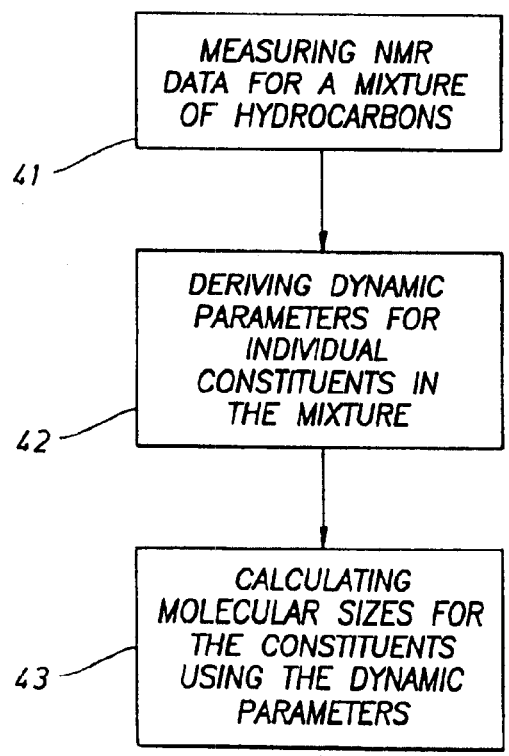
FIG. 5

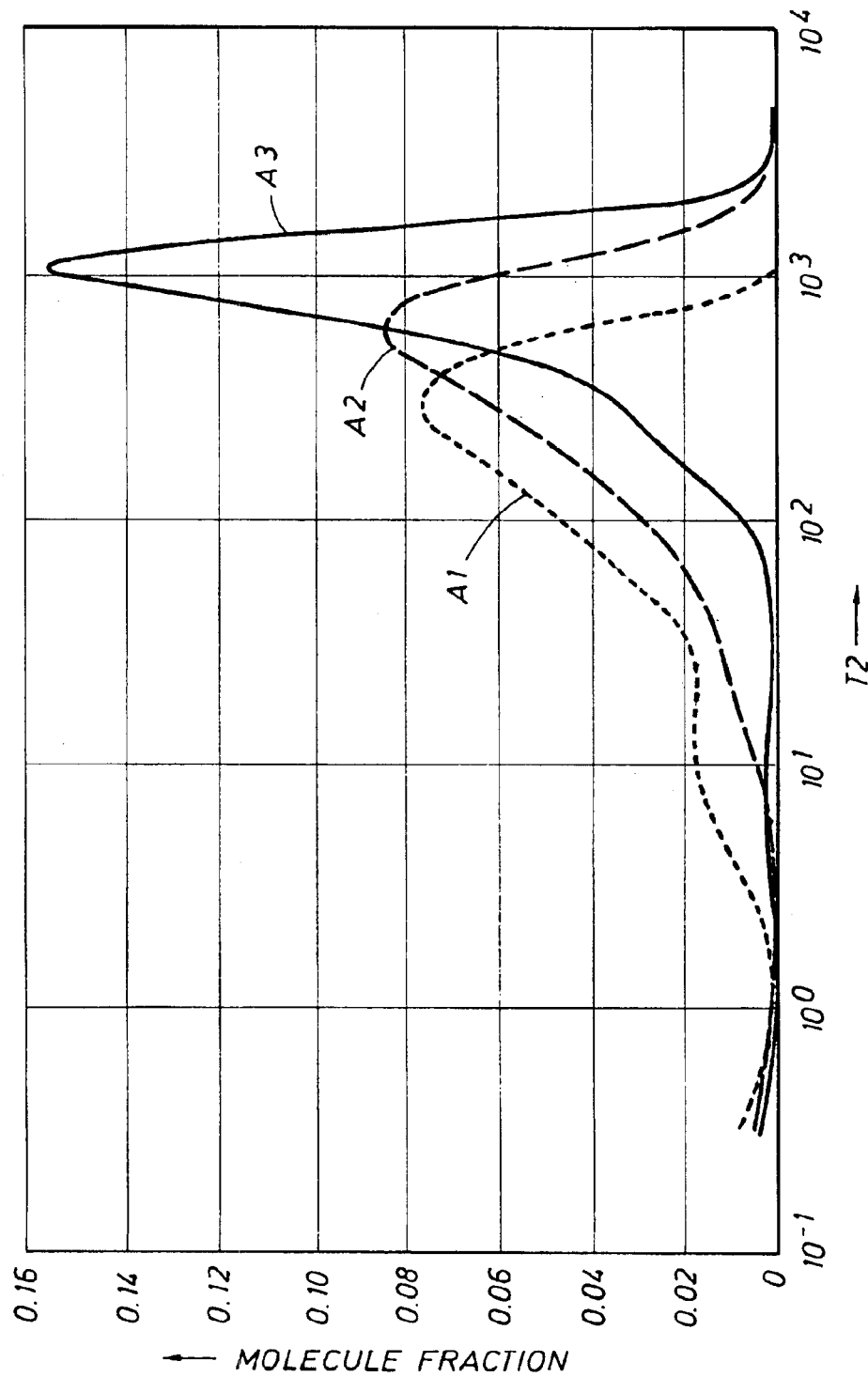

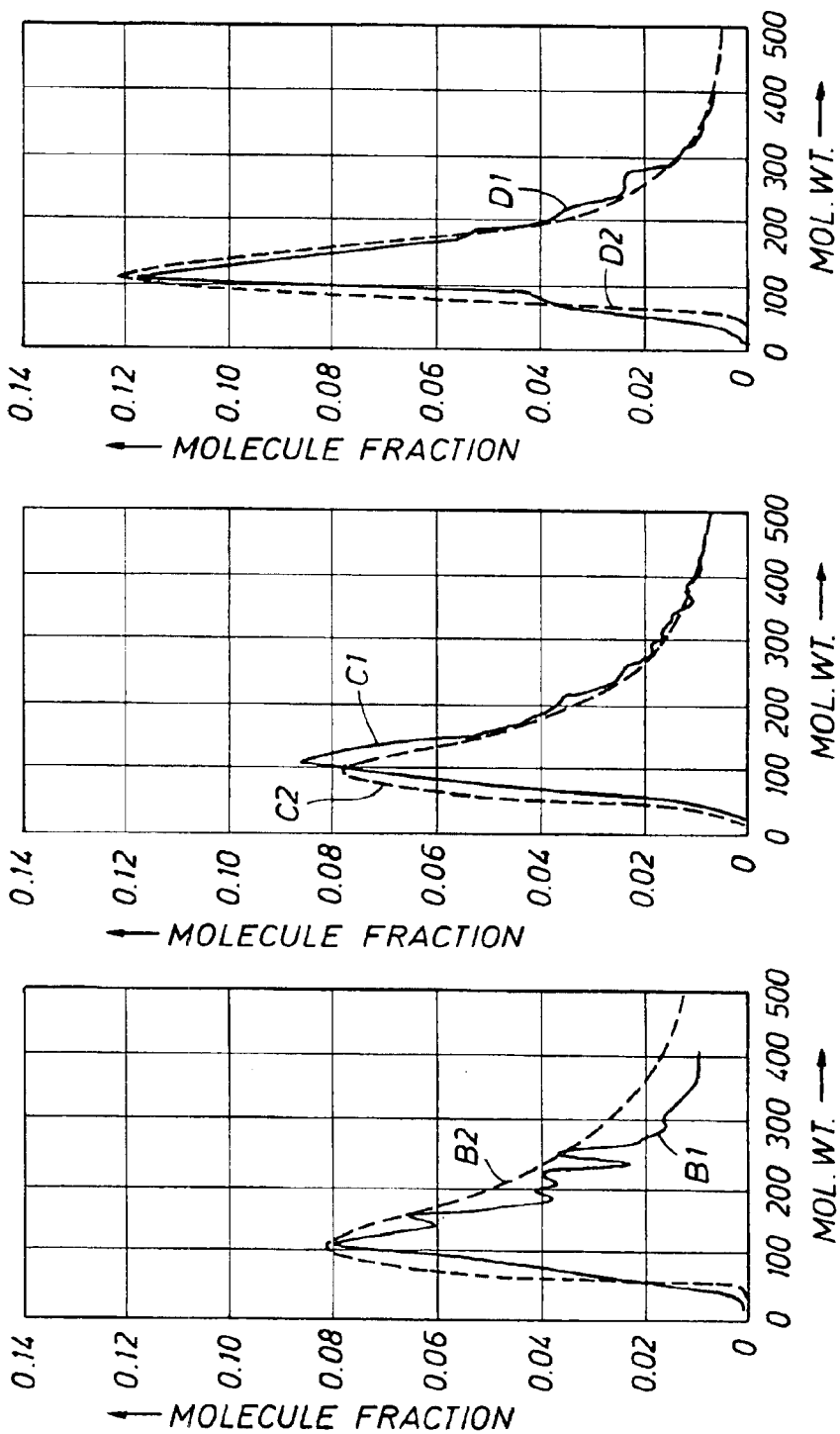

METHOD FOR DETERMINING MOLECULAR PROPERTIES OF HYDROCARBON MIXTURES FROM NMR DATA

BACKGROUND OF INVENTION

1. Field of the Invention

The present invention is related to the field of data processing methods for oil well logging and sampling. More specifically, the present invention relates to methods for determining properties of hydrocarbon mixtures and crude oils including molecular composition, molecular size, molecular weight, and molecular carbon number using nuclear magnetic resonance (NMR) data.

2. Background Art

Oil well logging and sampling tools include nuclear magnetic resonance (NMR) instruments. NMR instruments can be used to determine properties of earth formations, such as the fractional volume of pore space, the fractional volume of mobile fluid filling the pore space, and the porosity of earth formations. In addition, NMR data may be used to assess the content of brine and hydrocarbons in the formation. General background of NMR well logging is described in U.S. Pat. No. 6,140,817, assigned to the assignee hereof.

The signals measured by nuclear magnetic resonance (NMR) logging tools typically arise from the selected nuclei present in the probed volume. Because hydrogen nuclei are the most abundant and easily detectable, most NMR logging tools are tuned to detect hydrogen resonance signals (from either water or hydrocarbons). These hydrogen nuclei have different dynamic properties (e.g., diffusion rate and tumbling/rotation rate) that are dependent on their environments, such as the chemical structure and size of the molecules in which they reside. The different dynamic properties of these nuclei manifest themselves in different nuclear spin relaxation times (i.e., spin-lattice relaxation time (T1) and spin-spin relaxation time (T2); spin-lattice relaxation is also referred to as longitudinal relaxation, and spin-spin relaxation as transverse relaxation). For example, molecules in viscous oils cannot diffuse or tumble as fast as those in light oils. As a result, they have relatively short relaxation times. These observations suggest that NMR data (e.g., relaxation times) can provide information on molecular properties of hydrocarbons in the earth formations.

SUMMARY OF INVENTION

One aspect of the invention relates to methods for estimating molecular properties such as composition, size, carbon number and weight in a mixture (e.g., crude oils) from NMR data. A method for determining molecular properties in a mixture of hydrocarbons includes measuring NMR data of the mixture using an NMR tool or a laboratory NMR instrument; deriving at least one parameter for each observed constituent in the mixture from the NMR data; and calculating a molecular property for each observed constituent in the mixture from the at least one parameter. Methods according to some embodiments of the invention use correlations between relaxation times and molecular properties and/or between diffusion rates and molecular properties.

Other aspects of the invention would become apparent from the following description, the drawings, and the claims.

BRIEF DESCRIPTION OF DRAWINGS

FIG. 4 is a diagram illustrating a common pulse sequence for measuring transverse relaxation times of NMR signals and the resultant spin echoes that can be used to derive transverse relaxation times of nuclear magnetic signals.

FIG. 5 shows a flow chart of steps involved in the methods according to embodiments of the invention.

FIG. 6 shows results of estimating molecular sizes in mixtures using methods of the invention as compared with those from gas phase chromatography.

DETAILED DESCRIPTION

Figures 1, 2:
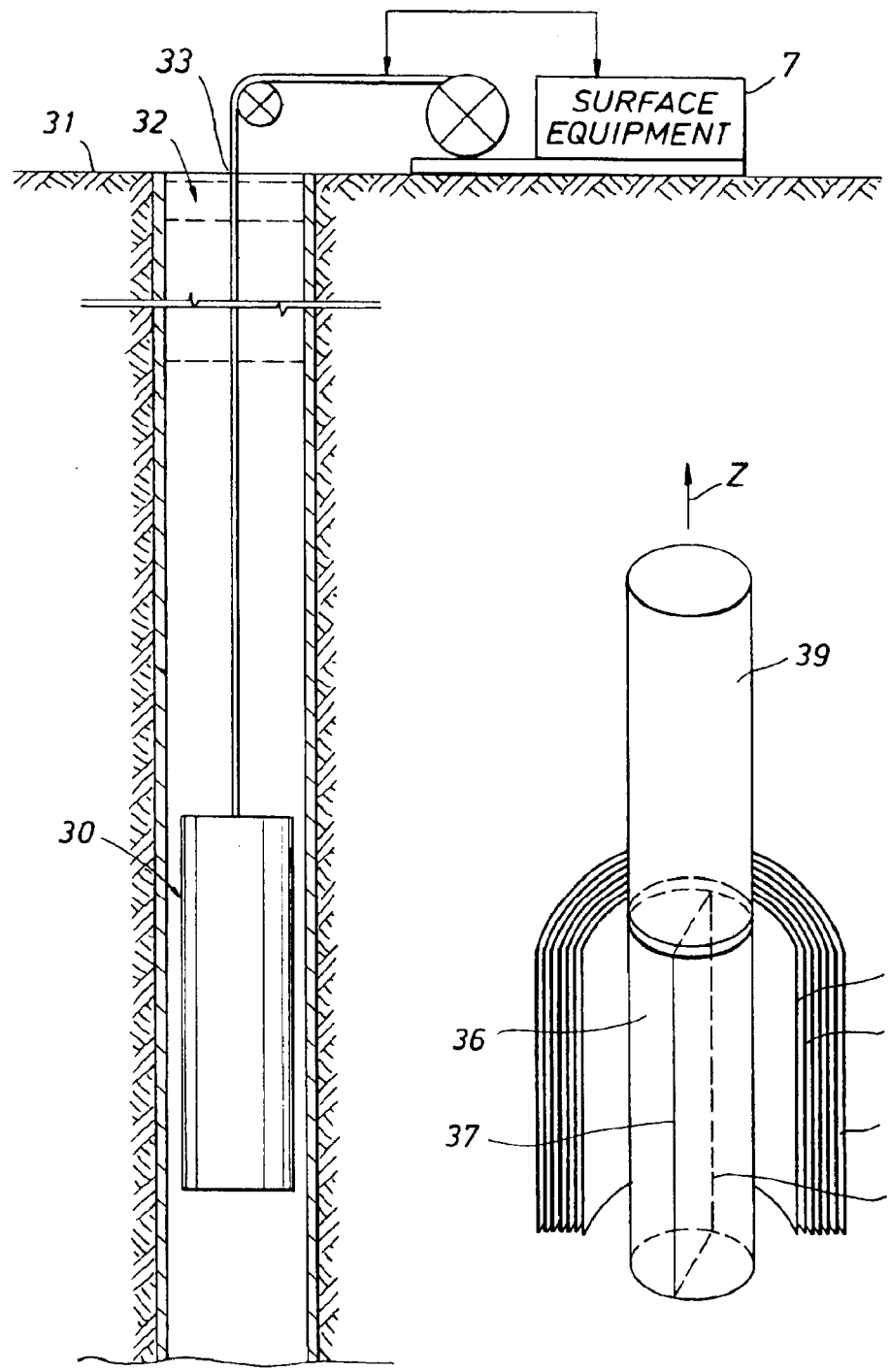
FIG. 1 is a diagram of a nuclear magnetic resonance tool in a borehole penetrating earth formations.
FIG. 2 is a diagram illustrating components of a nuclear magnetic resonance tool.

FIG. 1 shows a nuclear magnetic resonance (NMR) logging tool 30 for investigating earth formations 31 traversed by a borehole 32. The NMR logging device 30 is suspended in the borehole 32 on an armored cable 33, the length of which substantially determines the relative depth of the device 30. The cable length is controlled by suitable means at the surface such as a drum and winch mechanism (not shown). Surface equipment 7 can be of conventional type and can include a processor subsystem which communicates with downhole equipment including NMR logging device 30.

The NMR logging device 30 can be any suitable nuclear magnetic resonance logging device; it may be one for use in wireline logging applications as shown in FIG. 1, or one that can be used in logging while drilling (LWD) applications. The NMR logging device 30 typically includes a means for producing a static magnetic field in the formations, and a radio frequency (RF) antenna means for producing pulses of magnetic field in the formations and for receiving the spin echoes from the formations. The means for producing a static magnetic field may comprise a permanent magnet or magnet array, and the RF antenna means for producing pulses of magnetic field and receiving spin echoes from the formations may comprise one or more RF antennas.

A schematic representation of some of the components of an NMR logging device 30 is illustrated in FIG. 2, which shows a first centralized magnet or magnet array 36 and an RF antenna 37, which may be a suitably oriented coil or coils. FIG. 2 also illustrates a general representation of closely-spaced cylindrical thin shells, 38-1, 38-2 . . . 38-N, that can be frequency selected in a multi-frequency logging operation. One such device is disclosed in U.S. Pat. No. 4,710,713. In FIG. 2, another magnet or magnet array 39 is shown. Magnet array 39 may be used to pre-polarize the earth formation ahead of the investigation region as the logging device 30 is raised in the borehole in the direction of arrow Z. Examples of such devices are disclosed in U.S. Pat. Nos. 5,055,788 and 3,597,681.

Figure 3:
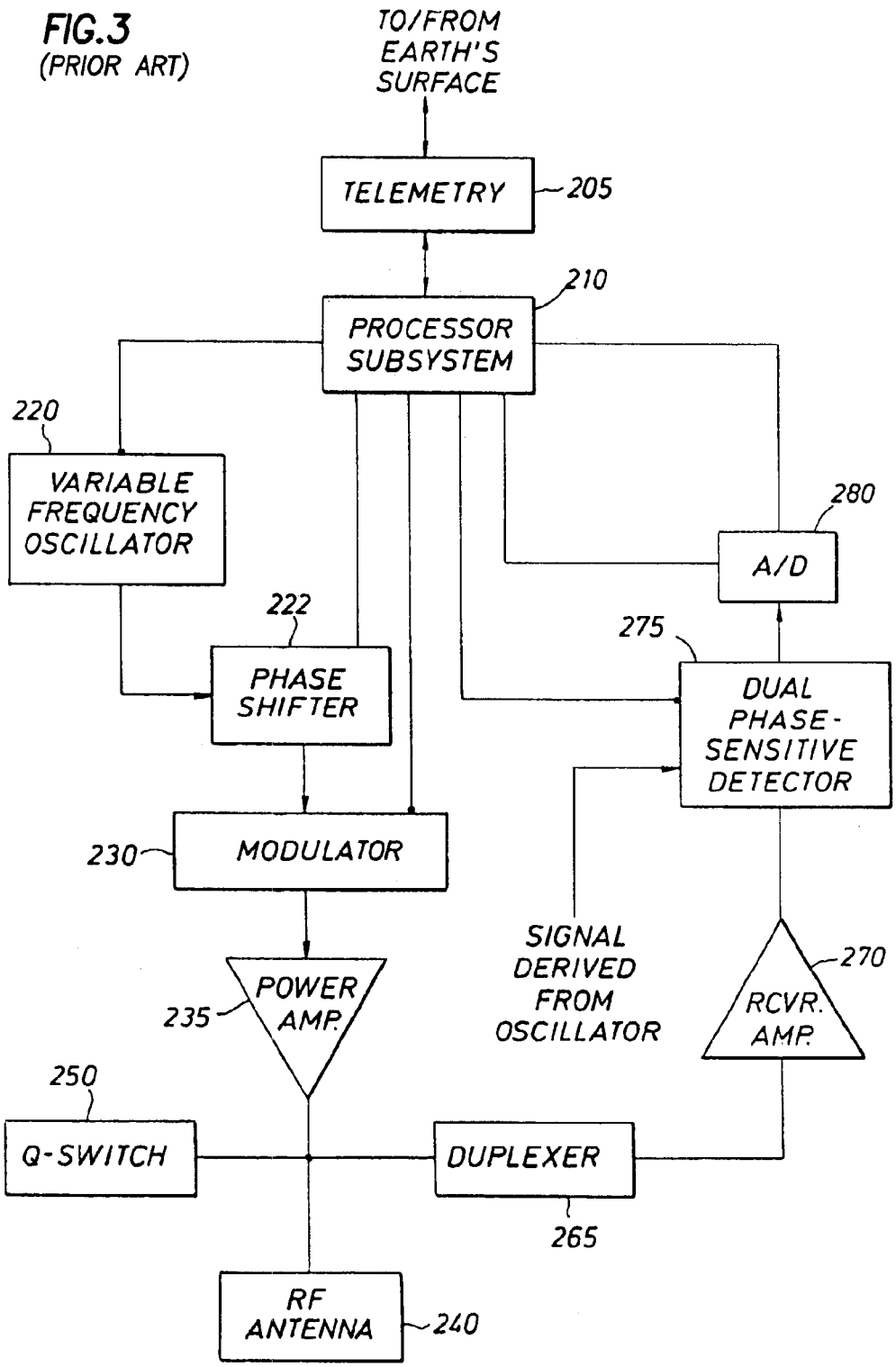
FIG. 3 illustrates a schematic diagram of a circuitry of an NMR tool for producing the RF pulses and for receiving and storing the spin echoes.

FIG. 3 illustrates a schematic of a circuitry of an NMR tool for producing the RF pulses and for receiving and storing the spin echoes. One skilled in the art would appreciate that any other suitable circuitry could be used without departing from the scope of the invention.

In FIG. 3, a downhole processor 210 has associated memory, timing, interfaces, and peripherals (not separately shown), as known in the art. The processor subsystem 210 is coupled with telemetry circuitry 205, for communication with a processor on the surface (not shown). The pulse forming circuitry includes a variable frequency oscillator 220 which, under control of processor 210, produces radio frequency (RF) signals at the desired frequencies. The output of oscillator 220 is coupled to a phase shifter 222 and then to a modulator 230, both of which are under the control of processor subsystem 210. The phase shifter 222 and modulator 230 can be controlled, in a manner known in the art, to produce the desired pulses of RF field, for example the 90 degree and 180 degree pulses for Carr-Purcell-Meiboom-Gill (CPMG) types of sequences or any other desired NMR pulse sequences. The output of modulator 230 is coupled, via a power amplifier 235, to the RF antenna 240. A Q-switch 250 can be provided to damp the RF antenna system to reduce antenna ringing. The antenna 240 is also coupled with a receiver section via duplexer 265, the output of which is coupled to receiver amplifier 270. The duplexer 265 protects the receiver amplifier 270 from the high power pulses which pass to the RF antenna 240 during the transmitting and damping modes. During the receiving mode, the duplexer 265 acts as a low impedance connection from antenna 240 to the receiver amplifier 270. The output of receiver amplifier 270 is coupled to a dual phase-sensitive detector 275, which also receives, as a reference, a signal derived from the oscillator signal. The detected output is coupled to analog-to-digital converter 280, the output of which is a digital version of the received nuclear magnetic resonance signal. Although the logging device or tool 30 is shown as a single body in FIG. 1, it may alternatively comprise separate components, and the tool may be combinable with other logging tools. Also, while a wireline is illustrated, alternative forms of physical support and communicating link can be used, for example in a measurement while drilling system.

Several NMR parameters may be measured that can be used to derive formation properties. Most NMR logging operations measure the spin-lattice (longitudinal) relaxation times (T1) and/or spin-spin (transverse) relaxation times (T2) of hydrogen nuclei. In addition, some NMR logging tools may provide a ratio of T1/T2 directly, and other NMR tools may provide diffusion constants (D). These NMR data (T1, T2, T1/T2, and D) are all applicable to the embodiments of the present invention, though the following discussion uses T2 relaxation times to illustrate the present invention.

Various pulse sequences are available for measuring the NMR relaxation times. For example, T1 relaxation may be measured using an inversion-recovery or a simple spin-echo pulse sequence or any of their derivatives. The T2 relaxation is often measured from a train of spin-echoes that are generated with a series of pulses such as the Carr-Purcell-Meiboom-Gill (CPMG) pulse sequence or some variant of this. The CPMG pulse sequence is well known in the art. (See Meiboom, S., Gill, D., 1958, "Modified Spin Echo Method for Measuring Nuclear Relaxation Times," Review of Scientific Instruments, 29, 688–91). As illustrated in FIG. 4, the CPMG pulse sequence generates a train of spin echoes, whose amplitudes exponentially decay as a function of time. The exponential decay life time is referred to as a transverse relaxation time, T2. Thus, T2 measurements are accomplished by analyzing the amplitudes of spin echoes thus obtained.

As shown in FIG. 4, in a CPMG sequence, the first RF pulse applied to antenna (37 in FIG. 2) is a 90-degree pulse, which reorients the hydrogen nuclei onto a plane ("transverse plane") perpendicular to the static magnetic field produced by the permanent magnet 36. Shortly after the initial 90-degree pulse, a train of 180-degree pulses (with a delay time between the successive 180-degree pulses, $T_{180}$, approximately twice as long as the initial delay between the 90-degree and the first 180-degree pulses, $T_{90}$) is applied to the antenna (37 in FIG. 2). Each of these 180-degree pulses results in a spin echo—a growth and subsequent decay of the detected signal magnitudes. During these measurements, the nuclear spins in the transverse plane gradually decrease amplitudes due to spin-spin interaction and other relaxation mechanisms. Consequently, each successive spin-echo has a lower amplitude than that of the preceding one. T2 relaxation time (the transverse relaxation time) information is then derived from analysis of the exponential decay profile.

Once NMR data (e.g., T1, T2 relaxation times, T1/T2 ratio, or diffusion rates) are collected, they are analyzed with an inversion method to derive the earth formation information. Any of the inversion methods known in the art are suitable. For example, U.S. Pat. No. 5,291,137, issued to Freedman and assigned to the same assignee hereof, discloses a "windows" processing method. This "window" processing method is suitable for most NMR data analysis.

Transverse (T2) relaxation in liquid is mainly through dipole-dipole interactions, which are influenced by the dynamic properties of the molecules (e.g., diffusion rates and molecular tumbling rates) and the fluids (e.g., viscosity). Thus, NMR data (especially, T2) may be used to provide information on the compositions of the fluids and the properties of the constituents (e.g., molecular sizes). While NMR data can be used to provide detailed information on individual constituents and their properties, most prior art NMR data analysis methods only focus on macroscopic properties of earth formation, such as where the hydrocarbon and brine zones are, porosity of the earth formations, and fractional volumes of pore space; few have focused on a more detailed analysis of properties of individual constituents (e.g., molecular size distributions) within a particular fluid.

As discussed earlier, NMR relaxation rates are dependent on dynamic properties of the molecules and the fluids. Thus, NMR data may be used to derive the diffusion rates and tumbling rates of the molecules. Because the molecular diffusion rates and tumbling rates are sensitive to molecular sizes as well as viscosity of the fluids, NMR data may be used to derive information concerning the composition of crude oils in terms of molecular sizes. Determining molecular property information from NMR data requires the relaxation time and/or diffusion rate distributions of the hydrocarbon fraction of the reservoir and/or borehole fluids. A suitable technique for obtaining these distributions in mixtures containing both hydrocarbons and water is the Magnetic Resonance Fluid (MRF) characterization method as disclosed in U.S. Pat. No. 6,229,308 B1 issued to Freedman. This patent is assigned to the same assignee hereof and is hereby incorporated by reference.

The MRF method invokes a Constituent Viscosity Model (CVM), which relates relaxation time and diffusion rates to constituent viscosities whose geometric mean is identical to the macroscopic fluid viscosity. The validity of the CVM was established by Freedman et al. using laboratory data acquired on live and dead hydrocarbon mixtures and crude oils. These results were reported by Freedman et al. in paper number 63214 entitled *"A New NMR Method of Fluid Characterization in Reservoir Rocks: Experimental Confirmation and Simulation Results"* presented at the 2000 Society of Petroleum Engineers Annual Technical Conference and Exhibition meeting.

While the MRF method would be used as an example in the following discussion of how to derive NMR parameters for individual constituents, one skilled in the art will appreciate that other similar methods may be used without departing from the scope of the invention. In situations where uncontaminated hydrocarbon samples are available, NMR parameters such as relaxation time and diffusion rate distributions may be estimated without applying the MRF method.

Using the CVM, the MRF method is capable of deriving distribution of constituent viscosities in fluid mixtures containing crude oils. The constituent viscosities are directly related to the distribution of NMR relaxation times measured on bulk crude oil samples and they reflect the complex composition of crude oils as a mixture of many different types of hydrocarbon molecules. The use of constituent viscosities simplifies the inversion by providing a single set of parameters for characterizing the crude oil distributions of bulk relaxation times and diffusion constants. The MRF technique provides improvements in all aspects of the standard NMR analysis, including estimates of total porosity, free-fluid and bound-fluid porosity, T2 distributions, and permeability in shaly sands.

In deriving constituent viscosities, the MRF method uses a general spin-echo relaxation model for a formation containing brine, hydrocarbons, and oil-based mud filtrate (OBMF). OBMF is commonly used in drilling the borehole. As shown in FIG. 4, amplitudes of the spin echoes in an NMR measurement decay exponentially as a function of time. Let AP represent the amplitude of the j-th echo acquired during measurement p. Consider the following general relaxation model, $$A_j^P = \sum_{l=1}^{N_\delta} a_l \exp\left(-\frac{j*TE_p}{T_{2,l}^+(p)}\right)\left(1 - \exp\left(-\frac{W_p}{\xi * T_{2,l}}\right)\right) + \\ \sum_{k=1}^{N_o} b_k \exp\left(-\frac{j*TE_p}{T_{2,o}^+(\eta_k, p)}\right)\left(1 - \exp\left(-\frac{W_p}{T_{1,o}(\eta_k)}\right)\right) + \\ A_{OBMF} \exp\left(-\frac{j*TE_p}{T_{2,OBMF}^+(p)}\right)\left(1 - \exp\left(-\frac{W_p}{T_{1,OBMF}}\right)\right)$$

(1)

where the first, second, and third terms are brine, hydrocarbons, and OBMF signals, respectively. This three-phase model explicitly accounts for contributions from individual constituents in brine and hydrocarbon phases, but only assumes an average relaxation time distribution in the OBMF phase. The simplified term for OBMF is justified because experimental measurements in OBMF have shown that NMR relaxation time distributions for individual constituents in OBMF are very narrow and can be described by a single exponential.

The apparent transverse (dipole-dipole) relaxations in any of the three phases modeled in Equation (1) include inherent transverse relaxation and relaxation due to self diffusion of molecules in the static magnetic field gradient $G_p$. For unrestricted diffusion in a uniform magnetic field gradient in the brine, the apparent transverse relaxation rates can be written as, $$\frac{1}{T_{2,l}^+(p)} = \frac{1}{T_{2,l}} + \frac{(\gamma_H * G_p * TE_p)^2}{12} D_w(T)$$

(2)

Here, $T_{2,l}$ in the first term on the right-hand side are a set of relaxation times that represent the sum of surface and bulk relaxation of the brine phase. The second term is the contribution to the relaxation rate from diffusion, where $\gamma_H = 2\pi*4258$ G$^{-1}$ s$^{-1}$ is the proton gyromagnetic ratio and $D_w(T)$ is the temperature dependent self diffusion coefficient of water in units of cm$^2$/s. Note that Equation (2) assumes an unrestricted diffusion and a uniform magnetic field gradient $G_p$. One skilled in the art will appreciate that corrections to $D_w(T)$ for the effects of restricted diffusion and to $G_p$ for the effects of internal rock gradients can be applied if appropriate.

Similarly, the apparent transverse relaxation rates in the native oil ($T_{2,o}$ ($\eta_k$,p)) can be written in the form, $$\frac{1}{T_{2,o}(\eta_k, p)} = \frac{1}{T_{2,o}(\eta_k)} + \frac{(\gamma_H * G_p * TE_p)^2}{12} D_o(\eta_k)$$

(3)

where $T_{2,o}(\eta_k)$ is the bulk relaxation time associated with amplitude $b_k$ in the hydrocarbon relaxation time distribution, and $D_o(\eta_k)$ is a viscosity dependent diffusion constant. The hydrocarbon (crude oil) is usually a non-wetting phase and is not affected by surface relaxation. Crude oils are mixtures consisting of many different types of hydrocarbon molecules of varying sizes, shapes and molecular weights. See, for example, McCain, W. D., *The Properties Of Petroleum Fluids*, Penn Well Publishing Co., Second Edition, Chapter 1, 1990. A molecular-level distribution of constituent viscosities ($\eta_k$) is assumed to exist in crude oils. This assumption is based on experimental data that there exists a distribution of relaxation times in crude oils.

The measured viscosity ($\eta_o$) reflects a macroscopic transport property of the crude oil that determines its flow properties and is the quantity that is used in hydrodynamic transport equations like the Navier-Stokes equation. Morriss et al showed that, for a suite of dead (i.e., not containing dissolved solution gas) crude oils, there exists a strong correlation between the logarithmic mean relaxation times of their constituents and the measured viscosities. See Morriss et al., *Hydrocarbon Saturation And Viscosity Estimation From NMR Logging In The Belridge Diatomite*, Paper C presented at the 35th Annual Meeting Of The Society Of Professional Well Logging Analysis, 1994. The macroscopic viscosity ($\eta_o$) of live crude oils is empirically related to the logarithmic mean (($\overline{T}_{2,o}$)$_{logm}$) of the transverse relaxation time distributions by a constitutive equation of the form, $$\frac{1}{(\overline{T}_{2,o})_{logm}} = \frac{a\eta_o f(GOR)}{T} \equiv c\eta_o$$

(4)

where a is an empirically determined constituent constant that has been determined by Morriss, et al. to be around 250 (i.e., a≈250 Ks$^{-1}$cp$^{-1}$), for ($\overline{T}_{2,o}$)$_{logm}$ in seconds centipoise and T the temperature in degrees Kelvin. Thus, $$c \equiv \frac{af(GOR)}{T}.$$

The empirically derived function f(GOR) accounts for live oils (those containing dissolved solution gas) and has been discussed by Freedman et al. in paper number 63214 entitled "A New NMR Method of Fluid Characterization in Reservoir Rocks: Experimental Confirmation and Simulation Results" presented at the 2000 Society of Petroleum Engineers Annual Technical Conference and Exhibition meeting.

The $\eta_k$ in Equation (3) are microscopic viscosities that reflect the complex composition of crude oils. Analogously with the above equation, the constituent viscosities are assumed to be related to the components in the relaxation time distribution via the same equation, $$\frac{1}{T_{2,o}(\eta_k)} = \frac{a\eta_k f(GOR)}{T} \equiv c\eta_k \quad (5)$$

The logarithmic mean of relaxation time is defined as, $$(\overline{T}_{2,o})_{\log mn} = 10^{\sum_{k=1}^{N_o} \overline{b}_k \log(T_{2,o}(\eta_k))} \quad (6)$$

with $$\overline{b}_k = \frac{b_k}{\sum_{k=1}^{N_o} b_k},$$

where $b_k$ are the $N_o$ amplitudes in the crude oil bulk relaxation time distribution. Substituting Equations (4) and (5) into Equation (6) would yield the macroscopic viscosity of the crude oil, $\eta_o$, which is the logarithmic mean of the individual microscopic viscosities, $\eta_k$:

$$\eta_o = 10^{\sum_{k=1}^{N_o} \overline{b}_k \log(\eta_k)}$$

where $\overline{b}_k$ is the "concentration" of the mixture constituent with viscosity $\eta_k$. The macroscopic viscosity $\eta_o$ is similar to the high temperature limit for the viscosity of a mixture according to the "Arrenhius mixing rule" see A. Bondi, *Physical Properties of Molecular Crystals, Liquids, and Glasses*, pp. 348–349, 1968.

The dependence of the relaxation times on viscosity and temperature in Equations (4) and (5) is consistent with the experimental observations and theoretical predictions of Bloembergen, Purcell, and Pound, *Relaxation Effects in Nuclear Magnetic Resonance Absorption*, Physical Review, vol. 73, no. 7, pp. 679–712, 1948.

Stokes-Einstein diffusion theory predicts that diffusivity is related to temperature and viscosity according to the equation: $D=kT/6\pi\eta R$, where k is the Boltzmann constant, R is the radius of the spherical particle, and T is the temperature in degrees Kelvin. Similar to the Stokes-Einstein equation, the self-diffusion constants for the crude oils, $D_o$, and for constituents in the crude oil, $D_o(\eta_k)$, are assumed to have the same dependence on $T/\eta_k$. Therefore, for crude oils, $$D_o = \frac{bT}{\eta_o} \times 10^{-5} \quad (7)$$

where b is a constant, $D_o$ is the measured crude oil diffusion constant in cm$^2$/s, and T is the temperature in degrees Kelvin. The empirical constitutive constant for crude oils, $b=5.05\times10^{-3}$ cm$^2$s$^{-1}$ cpK$^{-1}$, is given by Freedman et al. in paper number 63214 entitled "*A New NMR Method of Fluid Characterization in Reservoir Rocks: Experimental Confirmation and Simulation Results*," presented at the 2000 Society of Petroleum Engineers Annual Technical Conference and Exhibition meeting.

Analogously to the relationship between the macroscopic diffusion constant ($D_o$) and the macroscopic viscosity ($\eta_o$), the microscopic constituent diffusion constants of crude oil mixtures are related to the microscopic constituent viscosities (effective viscosities) according to the following equation:

$$D_o(\eta_k) = \frac{bT}{\eta_k} \times 10^{-5} \quad (8)$$

Equation (8) implies that there exists at the molecular level a distribution of diffusion constants in the crude oil mixture analogous to the distribution of relaxation times. These distributions of diffusion constants and relaxation times can be derived from the measured NMR data by iteratively fitting a model as shown in Equation (1) to these data using the method disclosed in U.S. Pat. No. 6,229,308 B1.

The above-described MRF method is just one way to obtain the distributions of the diffusion constants and the relaxation times. The MRF method is particularly appropriate when NMR data are obtained from mixed fluids (e.g., water, drilling fluid filtrates, and oil). If the oil sample is not contaminated with other fluids (e.g., crude oils), there would be no need to apply the MRF method to obtain the distributions of diffusion constants and the relaxation times.

Once the distribution of the diffusion constants and the relaxation times are estimated, they can be used to further derive the molecular properties of the individual constituents according to embodiments of the present invention. Molecular properties as used herein refer to molecular size, carbon number, and weight, i.e., those properties related to physical dimensions of the molecules. For example, assuming a spherical molecule with a radius of R, the individual diffusion constant is related to the radius R (hence, the molecular size) according to the Stokes-Einstein equation: $D_o=kT/6\pi\eta R$, where Do is the observed diffusion constant, k is the Boltzmann constant, T is the temperature in degrees Kelvin, and $\eta$ is the viscosity in centipoise.

Therefore, to derive molecular size information from the NMR data, the relaxation times ($T2_k$) and diffusion rates ($D_k$) of individual molecules (indexed by k) in a hydrocarbon mixture can be approximated as $$T2_k = \frac{a'(T)}{\eta^{\alpha'} f(GOR) N_k^{\beta'}} \quad (9)$$

$$D_k = \frac{b'(T)}{\eta^{\phi'} N_k^{\theta'}} \quad (10)$$

where $N_k$ is the number of carbon atoms in the kth constituent, a'(T) and b'(T) are functions of temperature, T, $\eta$ is the fluid viscosity, and $\alpha'$, $\beta'$, $\phi'$ and $\theta'$ are (as yet) unknown exponents. Note that these expressions are generalizations of the Stokes-Einstein and Bloembergen relations for diffusion and spin relaxation of spherical particles in liquids. Equation (9) includes a factor that represents the gas/oil ratio (GOR). This is included because it is known that GOR is an important parameter in determining the relaxation time dependence on viscosity and temperature. See Lo et al., *Relaxation Time And Diffusion Measurements of Methane And N-Decane Mixtures*, The Log Analyst, pp. 43–46, November–December, 1998; see also U.S. Pat. No. 6,229,308 B1. Within the context of the CVM approach, the denominators of Equations (9) and (10) are proportional to constituent viscosities.

With the approximations in Equation (9) and (10), it is tempting to assume that the exponents $\alpha'$ and $\phi'$ are equal to 1 and then make some correlation between $N_k$ and molecular "radius," R, to mimic the ideal spherical particle expressions. Such assumption suggests a dependence on the inverse of $\eta R$ for D and on the inverse of $\eta R^3$ for T2. However, this approach immediately fails for mixtures because it implies that the geometric mean of the $N_k$ distribution is independent of the details of the mixture. This contradiction follows directly when the expressions in Equations (4) and (7) are respectively substituted into the constituent Equations (9) and (10).

By incorporating empirical results concerning the relation between viscosity and the geometric mean relaxation times and diffusion rates, i.e., $T2_{LM}$ and $D_{LM}$ are linearly dependent on $T/\eta$, Equations (9) and (10) can be reformulated as, $$N_k = \frac{a(T)T2_{LM}^\alpha [f(GOR)]^{\alpha-1}}{T2_k^\beta} \quad (11)$$

$$N_k = \frac{b(T)D_{LM}^\phi}{D_k^\theta} \quad (12)$$

Note that Equations (11) and (12) are obtained from Equations (9) and (10) simply by introducing the empirical expressions, $T2_{LM}=a'T/\eta f(GOR)$ and $D_{LM}=b'T/\eta$, re-ordering the variables, and defining a new set of exponents (unprimed).

Equations (11) and (12) indicate that if the exponents, $\alpha$, $\beta$, $\phi$, and $\theta$, are known, the $N_k$ (carbon number) may be obtained from the geometric means of T2 and D (i.e., $T2_{LM}$ and $D_{LM}$). Because relationships shown in Equations (11) and (12) are not dependent on the exact natures of the individual constituents in the mixture, it should be possible to derive these exponents, $\alpha$, $\beta$, $\phi$, and $\theta$, using a simple model mixture system. Once these exponents are derived, they may be used in other systems of similar compositions.

As an example, rough estimates for the exponents, $\alpha$, $\beta$, $\phi$, and $\theta$, which would be useful in other hydrocarbon mixture systems, can be derived from an experimental mixture of squalene (C30) and hexane (C6). For this mixture, GOR=0 and f(GOR)=1. Data for the pure squalene (C30) and hexane (C6) and three mixtures of these two components at 30° C. are given in Table 1. Note that any suite of hydrocarbon samples, including crude oils, may be used to derive such parameters.

TABLE 1

Relaxation Time and Diffusion Rates for the Hexane-Squalene System

| Fluid (% C6) | $T2_{C30}$ (ms) | $T2_{C6}$ (ms) | $D_{C30}$ (cm$^2$s$^{-1}$) | $D_{C6}$ (cm$^2$s$^{-1}$) | $T2_{LM}$ (ms) | DLM (cm$^2$s$^{-1}$) | $\eta$ (cp) |
|---|---|---|---|---|---|---|---|
| 0   | 300  | —    | 1.0 × 10$^{-6}$ | —              | 300  | 1.0 × 106      | 11  |
| 38  | 900  | 4600 | 3.7 × 10$^{-6}$ | 1.3 × 10$^{-5}$ | 1670 | 6.0 × 10$^{-6}$ | 1.7 |
| 50  | 1180 | 5800 | 4.9 × 10$^{-6}$ | 1.7 × 10$^{-5}$ | 2610 | 9.1 × 10$^{-6}$ | 1.2 |
| 69  | 1690 | 7500 | 9.9 × 10$^{-6}$ | 3.0 × 10$^{-5}$ | 4780 | 2.7 × 10$^{-5}$ | 0.6 |
| 100 | —    | 9800 | —              | 4.6 × 10$^{-5}$ | 9800 | 4.6 × 10$^{-5}$ | 0.3 |

Once the T2, $T2_{LM}$, D, $D_{LM}$ values for squalene (C30) and hexane (C6) are available, they can be plugged into Equations (11) and (12) to produce the rough estimates of the exponents, $\alpha$, $\beta$, $\phi$, and $\theta$. From the dataset shown in Table 1, suitable exponents and pre-multiplying functions are determined, and the expressions for $N_k$ (at 30° C.) as shown in Equations (11) and (12) are simplified as:

$$N_k \approx \frac{650 T2_{LM}^{1/2}}{T2_k} \quad (13)$$

$$N_k \approx \frac{0.04 \times D_{LM}}{D_k^{3/2}} \quad (14)$$

Equations (13) and (14) can be used to estimate molecular sizes of individual constituents in a similar mixture. Using Equations (13) and (14) and the measured relaxation and diffusion data shown in Table 1, the $N_k$ values for the squalene-hexane system are given in Table 2.

TABLE 2

Number of Carbons Estimated for Squalene (C30) and Hexane (C6) from Relaxation Time (T2) and Diffusion Rate (D) Measurements

| Fluid (% C6) | $N_{C30}$ (T2) | $N_{C30}$ (D) | $N_{C6}$ (T2) | $N_{C6}$ (D) |
|---|---|---|---|---|
| 0   | 37 | 40 | —   | —   |
| 38  | 30 | 34 | 5.8 | 5.1 |
| 50  | 28 | 34 | 5.7 | 5.2 |
| 69  | 27 | 34 | 6.0 | 6.6 |
| 100 | —  | —  | 6.6 | 5.9 |

As shown in Table 2, reasonable values for $N_k$ can be obtained using either relaxation times or diffusion rates. It should be noted that Equations (13) and (14) and the example used here are merely intended to illustrate the basic concept of how to obtain these values; they should not limit the invention. One skilled in the art will appreciate that the derived exponents in the above example were rounded to give simple half-integer fractions for simplicity. Alternative optimized values may be derived which should provide better estimates for $N_k$. However, as shown in the above example, even with the simplified rough estimates, the $N_k$ values can be obtained with reasonable accuracy. Therefore, the rough estimate approach as shown here should be sufficient for most situations.

The pre-multipliers, 650 and 0.04, in Equations (13) and (14), respectively, in principle are valid only at the measurement temperature of 30° C. However, the temperature dependence of these values is relatively weak (approximately $T^{1/2}$ with T in degrees Kelvin). Thus, these values may be used in a temperature range around 30° C. For crude oils, the optimum exponents and pre-multipliers might differ slightly from those derived for simple bi-component mixtures. Equations (13) and (14) are not strictly compatible with the CVM equations because $T2_k$ and $D_k$ depend differently on $N_k$ and $\eta$. The diffusion constants $D_k$, as shown in Equation (14), exhibit a weaker dependency on $N_k$ than do the relaxation times, $T2_k$, as shown in Equation (13). This result agrees qualitatively with the ideal spherical particle relations. In view of the many approximations and assumptions implicit in this kind of model, any resulting "carbon number" (or molecular size) distribution should probably be regarded as an approximate indicator rather than a definitive and accurate breakdown of molecular composition.

Equations (9)–(12) should be regarded as particular implementations of the method. Alternative mathematical expression relating relaxation times and diffusion rates with molecular size, carbon number or other constituent property could also be derived and calibrated to hydrocarbon mixtures. It is also feasible to determine molecular properties from measured NMR data using model independent pattern recognition methods such as neural networks. In this approach, there are no model dependent equations (e.g., equations 13 and 14). Instead a "training data set" of molecular properties versus NMR and diffusion properties is used to train a neural network to predict molecular properties given NMR data on a sample outside of the training set. Any commercially available neural network software (such as that available from the Mathworks, Inc. at www.mathworks.com) may be adapted to determine molecular properties without the need to invoke model equations. These methods might also incorporate additional data derived from other measurements, for example NMR spectroscopy or optical analysis.

FIG. 5 summarizes steps involved in methods for evaluating molecular size distribution in a hydrocarbon mixture according to embodiments of the invention. First, NMR data are collected (process 41 in FIG. 5). This may be performed with any suitable NMR logging tool. For example, embodiments of the invention are applicable to wireline and while-drilling NMR tools as well as any suitable NMR module sampling tool such as the Modular Formation Dynamics Tester (MDT™ from Schlumberger Technology, Houston, Tex.). In fact, the absence of fluid-rock interactions, which complicate the MRF analysis for wireline or LWD-NMR tools, should lead to greater accuracy and robustness of the method in a sampling module or laboratory analysis Once the NMR data are collected, they are analyzed using an inversion method to derive individual constituent dynamic parameters (e.g., T1, T2, T1/T2, and diffusion constants; process 42 in FIG. 5). As discussed earlier, the MRF method or any similar method may be used for this purpose. Note that the MRF technique and the extension to it described herein are able to provide real-time information on reservoir fluids (e.g., viscosity, molecular composition) that at present can only be provided by lengthy pressure-volume-temperature (PVT) analysis performed in laboratories.

Finally, the individual constituent dynamic parameters (e.g., T1, T2, T1/T2, and diffusion constants) may be used to derive the molecular size information (process 43 in FIG. 5). As discussed above, the molecular sizes can be correlated with the transverse relaxation times and the diffusion constants according to Equations (11) and (12). The exponents in these equations can be estimated using a model mixture having similar components and/or properties (i.e., hydrocarbons) under similar conditions (e.g., temperature). Rough estimates of these components ("empirical parameters") would be sufficient. Having these exponents, Equations (11) and (12) may be simplified to those like Equations (13) and (14). The individual constituent dynamic parameters (e.g., T1, T2, T1/T2, and diffusion constants) in the mixture of interest derived from process 42 may then be used to calculate the molecular sizes of constituents (or their distribution in the mixture).

FIGS. 6A–6D illustrate results obtained with methods of the present invention as compared with those obtained with gas phase chromatography (GPC) that is commonly used in a PVT laboratory for such analysis. This example also illustrates that, in addition to wellsite applications, methods of the invention are equally applicable to standard laboratory analysis of crude oil samples.

FIG. 6A shows the T2 relaxation time distributions of three different dead crude oil samples. Curves A1–A3, representing samples 1–3, have geometric mean $T2_{LM}$ values of 105 ms, 239 ms, and 603 ms, respectively. These measurements were obtained at 300° K.

Curves A1–A3 were analyzed with methods of the invention and the resultant molecular weight distributions are shown as curves B2–D2 in FIGS. 6B–6D, respectively. These results were obtained using a(T)=170, T=300° K, $\alpha$=0.51, and $\beta$=0.90 in Equation (11). For comparison, the corresponding molecular weight distributions as obtained with GPC analysis are superimposed in FIGS. 6B–6D as curves B1–D1, respectively. It is clear from these figures that the NMR methods according to embodiments of the present invention produce results similar to those obtained from the GPC method. It should be noted that a GPC analysis takes several hours, while an NMR measurement takes only a few minutes. Furthermore, GPC analysis relies on correlation of component retention times with their molecular weight, which may be no more reliable than methods of the present invention. The NMR approach also has further advantages that it is non-destructive, and sample handling is relatively simple.

Although the example in FIG. 6 uses NMR transverse relaxation time (T2), one skilled in the art would appreciate that other NMR parameters (T1, T1/T2, or diffusion constant) may be used. Furthermore, while this example used a mixture of hydrocarbons (crude oils), methods of the invention may also be applied to other liquid mixtures.

While the invention has been described using limited examples, those skilled in the art, having the benefit of this disclosure, will appreciate that other methods can be devised without departing from the scope of the invention as disclosed herein. Accordingly, the scope of the invention should be limited only by the attached claims.

What is claimed is:

1. A method for determining a molecular property of each constituent in a mixture of hydrocarbons in a portion of earth formation surrounding a borehole comprising:
    generating a static magnetic field in a portion of earth formation surrounding a borehole;
    producing an rf magnetic field in the portion of earth formation;
    measuring nuclear magnetic resonance signals from the portion of earth formation;
    deriving at least one dynamic parameter for each constituent in the mixture from nuclear magnetic resonance signals, and
    calculating at least one molecular property selected from the list of molecular size distributions, molecular weight distributions and carbon number distributions for the mixture from the at least one dynamic parameter for each constituent.

2. The method of claim 1, wherein the deriving the at least one dynamic parameter comprises generating a model that includes a plurality of components for the constituents of the mixture and iteratively modifying the model components to optimize the model with respect to the nuclear magnetic resonance data.

3. The method of claim 1, wherein the at least one dynamic parameter comprises one selected from a longitudinal relaxation time, a transverse relaxation time, a ratio of longitudinal to transverse relaxation time, and a diffusion rate.

4. The method of claim 1, wherein the mixture of hydrocarbons is disposed in a geological formation.

5. The method of claim 1, wherein the calculating the molecular property for the each constituent in the mixture from the at least one dynamic parameter comprises correlating the at least one dynamic parameter of the each constituent with an effective viscosity of the each constituent.

6. The method of claim 5, wherein the correlating comprises deriving empirical parameters from a suite of hydrocarbon samples.

7. The method of claim 6, wherein the suite of hydrocarbon samples comprises crude oils.

8. The method of claim 1, wherein the calculating the molecular property comprises using a neural network.

9. A method for determining a molecular property of each constituent in a mixture of hydrocarbons in a portion of earth formation surrounding a borehole, comprising:
    generating a static magnetic field in a portion of earth formation surrounding a borehole;
    producing an rf magnetic field in the portion of earth formation;

measuring nuclear magnetic resonance signals from the portion of earth formation;

deriving at least one dynamic parameter for the each constituent in the mixture from the nuclear magnetic resonance signals; and calculating at least one molecular property selected from the list of molecular size distributions, molecular weight distributions and carbon number distributions for the mixture from the at least one dynamic parameter for the each constituent.

10. The method of claim 9, wherein the deriving the at least one dynamic parameter comprises generating a model that includes a plurality of components for the constituents of the mixture and iteratively modifying the model components to optimize the model with respect to the nuclear magnetic resonance data.

11. The method of claim 9, wherein the at least one dynamic parameter comprises one selected from a longitudinal relaxation time, a transverse relaxation time, a ratio of longitudinal to transverse relaxation time, and a diffusion rate.

12. The method of claim 9, wherein the mixture of hydrocarbons is disposed in a geological formation.

13. The method of claim 9, wherein the calculating the molecular property for the each constituent in the mixture from the at least one dynamic parameter comprises correlating the at least one dynamic parameter of the each constituent with an effective viscosity of the each constituent.

14. The method of claim 13, wherein the correlating comprises deriving empirical parameters from a suite of hydrocarbon samples.

15. The method of claim 14, wherein the suite of hydrocarbon samples comprises crude oils.

16. The method of claim 9, wherein the calculating the molecular property comprises using a neural network.

17. The method of claim 9, wherein the measuring nuclear magnetic resonance data comprises using one tool selected from a wireline nuclear magnetic resonance tool, a logging while-drilling nuclear magnetic resonance tool, and a modular formation dynamics tester or a laboratory nuclear magnetic resonance instrument.

18. A method of well logging comprising:

moving a nuclear magnetic resonance tool along a wellbore;

generating a static magnetic field in a portion of earth formation;

producing an rf magnetic field in the portion of earth formation; making nuclear magnetic resonance measurements of a mixture of hydrocarbons in the portion of earth formation;

deriving at least one dynamic parameter for each constituent in the mixture from the nuclear magnetic resonance measurements; and calculating at least one molecular property selected from the list of molecular size distributions, molecular weight distributions and carbon number distributions for the mixture from the at least one dynamic parameter for each constituent.

19. The method of claim 18, wherein the deriving the at least one dynamic parameter comprises generating a model that includes a plurality of components for the constituents of the mixture and iteratively modifying the model components to optimize the model with respect to the nuclear magnetic resonance measurements.

20. The method of claim 18, wherein the at least one dynamic parameter comprises one selected from a longitudinal relaxation time, a transverse relaxation time, a ratio of longitudinal to transverse relaxation time, and a diffusion rate.

21. The method of claim 18, wherein the calculating the molecular property for the each constituent in the mixture from the at least one dynamic parameter comprises correlating the at least one dynamic parameter of the each constituent with an effective viscosity of the each constituent.

22. The method of claim 21, wherein the correlating comprises deriving empirical parameters from a suite of hydrocarbon samples.

23. The method of claim 22, wherein the suite of hydrocarbon samples comprises crude oils.

24. The method of claim 18, wherein the calculating the molecular property comprises using a neural network.

25. The method of claim 18, wherein the nuclear magnetic resonance tool comprises one selected from a wireline nuclear magnetic resonance tool, a logging while-drilling nuclear magnetic resonance tool, and a modular formation dynamics tester.

26. A method for determining molecular property distribution in a liquid sample, comprising:

obtaining in a downhole sampling tool a liquid sample from a earth formation;

performing nuclear magnetic resonance measurements on the liquid sample;

determining a nuclear magnetic resonance parameter distribution of the liquid sample, wherein the nuclear magnetic resonance parameter comprises one selected from longitudinal relaxation time, transverse relaxation time, a ratio of longitudinal to transverse relaxation time, and a diffusion rate; and calculating eat least one molecular property selected from the list of molecular size distributions, molecular weight distributions and carbon number distributions for the liquid sample from the nuclear magnetic resonance parameter distribution.

27. The method of claim 26, wherein the calculating comprises correlating the nuclear magnetic resonance parameter of each constituent in the liquid sample with an effective viscosity of the each constituent.

28. The method of claim 27, wherein the correlating comprises deriving empirical parameters from a suite of hydrocarbon samples.

29. The method of claim 28, wherein the suite of hydrocarbon samples comprises crude oils.

30. The method of claim 26, wherein the calculating comprises using a neural network.

31. The method of claim 26, wherein the liquid sample comprises hydrocarbons.

\* \* \* \* \*